(12) United States Patent
Shelley et al.

(10) Patent No.: US 7,767,970 B2
(45) Date of Patent: Aug. 3, 2010

(54) METHOD FOR PERFORMING IR SPECTROSCOPY MEASUREMENTS TO DETERMINE FILM COATING THICKNESS ON A SUBSTRATE

(75) Inventors: Paul H. Shelley, Lakewood, WA (US); Gregory J. Werner, Puyallup, WA (US)

(73) Assignee: The Boeing Company, Chicago, IL (US)

( * ) Notice: Subject to any disclaimer, the term of this patent is extended or adjusted under 35 U.S.C. 154(b) by 53 days.

(21) Appl. No.: 12/189,086

(22) Filed: Aug. 8, 2008

(65) Prior Publication Data

US 2010/0032572 A1  Feb. 11, 2010

(51) Int. Cl.
*G01J 5/02* (2006.01)
(52) U.S. Cl. .................................................. 250/341.8
(58) Field of Classification Search ............... 250/341.8
See application file for complete search history.

(56) References Cited

U.S. PATENT DOCUMENTS

| | | | | |
|---|---|---|---|---|
| 3,994,586 | A * | 11/1976 | Sharkins et al. ............... | 356/73 |
| 4,129,781 | A * | 12/1978 | Doyle ....................... | 250/341.3 |
| 6,310,348 | B1 * | 10/2001 | Melling et al. ........... | 250/341.2 |
| 6,784,431 | B2 | 8/2004 | Shelley et al. | |
| 6,794,651 | B2 | 9/2004 | Shelley et al. | |
| 6,903,339 | B2 | 6/2005 | Shelley et al. | |
| 7,115,869 | B2 | 10/2006 | Shelley et al. | |
| 7,223,977 | B2 | 5/2007 | Shelley et al. | |
| 2002/0113212 | A1 * | 8/2002 | Meglen et al. ......... | 250/339.05 |

\* cited by examiner

*Primary Examiner*—David P Porta
*Assistant Examiner*—Marcus H Taningco
(74) *Attorney, Agent, or Firm*—Tung & Associates

(57) ABSTRACT

A method of determining a film coating thickness on a substrate including making near-IR spectra of a series of coating thickness or coating weight standards on an appropriate substrate material to match sample material in question, pre-processing the data to prepare it for multivariate calibration methods, performing the multivariate calibration, saving the calibration model in the hand-held near-IR device in an appropriate format, and using the calibration model to predict sample material thickness in question from their near IR spectra.

21 Claims, 5 Drawing Sheets

METHOD FOR PERFORMING IR SPECTROSCOPY MEASUREMENTS TO DETERMINE FILM COATING THICKNESS ON A SUBSTRATE

FIELD OF THE INVENTION

This invention generally relates to Infrared (IR) measurement methods and apparatus, and more particularly provides a method for performing non-destructive Near-IR spectroscopy measurements of surface characteristics of materials including determining a thickness of a film coating on a substrate, including epoxy bond primer thickness on a metallic substrate, and including use of a flexible fiber optic optical probe for difficult to reach locations.

BACKGROUND OF THE INVENTION

IR spectroscopy measurements may be useful for a variety of purposes including aerospace, automotive and industrial applications, as well as biological and bio-medical applications. For example, infrared (IR) radiation is readily absorbed by materials in association with relative motions (vibrations) of atoms such as carbon, hydrogen, oxygen and nitrogen. As such, IR spectroscopy measurements may indicate a condition of a wide variety of organic as well as inorganic materials.

For example, frequently it is necessary to determine the thickness of a coating material on a substrate, to verify that the film coating thickness is sufficiently thick, but not too thick, including but not limited to, bond primer film thicknesses on a metallic substrate. It is frequently necessary to measure surfaces that are the inner walls of a tube or fitting and for that a flexible fiber optic measurement is needed. Near-IR spectrometers generally work well with fiber optic probes One problem with determining the thickness of thin films on substrates may include the fact that the surface may include surface roughness, making surface contact methods that contact the surface over the scale of the roughness, such as eddy current measurement methods, inadequate. In addition, the film may be sufficiently thin to make prior art methods such as eddy current detection and ultrasound methods inadequate.

Other infrared(IR) non-destructive methods in the prior art used to measure the properties of thin films include using IR absorbance to determine the amount of a chromated conversion coating on a metallic substrate (U.S. Pat. No. 6,794,631), determining the amount of an anodize coating on a metallic substrate, (U.S. Pat. No. 6,784,431), determining an amount of chemical cure and amount of surface contamination (U.S. Pat. No. 6,906,327), determining the amount/thickness of an opaque coating on a substrate (U.S. Pat. No. 6,903,339) and (U.S. Pat. No. 7,223,977), and determining an amount of heat damage to a resin-fiber composite substrate (U.S. Pat. No. 7,115,869), all of which are fully incorporated by reference herein.

None of the above methods and associated devices, however, disclose a method or device that is suitable for performing IR spectroscopy including determining a thickness of a film coating on a substrate, particularly where a portable, real-time capability is desirable, and the inner surfaces of a tube or fitting needs to be measured, such as in aircraft manufacturing, assembly, maintenance, and repair of aircraft.

Thus, there is a continuing need for improved IR non-destructive testing methods including a method that is suitable for performing IR spectroscopy to determine a thickness of a film coating on a substrate, including a portable, real-time near-IR spectroscopic method with a flexible fiber optic probe, advantageously usable in aircraft manufacturing, assembly, maintenance, and repair of aircraft.

Therefore it is an object of the invention to provide a method that is suitable for performing IR spectroscopy to determine a thickness of a film coating on a substrate, including a portable, real-time near-IR spectroscopic method with a flexible fiber optic probe, advantageously usable in aircraft manufacturing, assembly, maintenance, and repair of aircraft.

SUMMARY OF THE INVENTION

The present invention includes methods of determining a film coating thickness on a substrate including obtaining the spectra of a series of film coating thickness (or weight) standards and building a multivariate calibration model with the spectra of those standards. An infrared spectrum obtained from the coating film which is in question can then be predicted by the multivariate model to determine the thickness of the film.

These and other objects, aspects and features of the invention will be better understood from a detailed description of the preferred embodiments of the invention which are further described below in conjunction with the accompanying Figures.

BRIEF DESCRIPTION OF THE DRAWINGS

FIG. 28 shows pre-processed near IR spectra using a first derivative and smoothing algorithm

DETAILED DESCRIPTION OF THE PREFERRED EMBODIMENT

The present invention achieves the foregoing objects, aspects and features by providing a method of non-destructively determining the thickness of a film coating on a substrate where the method may be accomplished by making an infrared (IR) spectroscopy measurement with an IR spectrometer over a spectrum of wavelengths in the near-IR, preferably with a portable near-IR spectrometer, often with a flexible fiber optic probe in hard to reach places, and performing multivariate calibration of near-IR spectra to a series of coating thickness (or coating weight) standards in order to generate a calibration model that can be used to predict the coating thickness (or coating weight) for samples in question including as part of a manufacturing, assembly, maintenance, or repair process of an aircraft.

It will be appreciated that although the invention is particularly explained with reference to using IR spectroscopy to determine a thickness of a bond primer film coating on roughened metallic surfaces used in portions of aircraft, that the invention may additionally be advantageously used to quantify a thickness of a film coating on a substrate in general, particularly roughened metallic substrates (surfaces).

While either a portable or non-portable IR spectrometer may be used to carry out the IR spectroscopy measurements according to the present invention, in a preferred embodiment a near-IR spectrum of wavelengths, e.g., including the range of about 1600 to about 2400 nanometers, is used to make the IR spectroscopy measurement according to the present invention. Further, in a preferred embodiment, a hand-held portable spectrometer capable of performing near-IR spectroscopy measurements is used to perform the IR spectroscopy measurements according to the present invention. The measurement is often performed with a flexible fiber optic probe and a separate calibration is needed when using the fiber optic probe. The term near-IR refers to a spectrum of wavelengths from about 1600 to about 2400 nanometers.

The hand-held portable IR spectrometer may have the capability to supply source IR energy to a sample at a predetermined incident angle between about 30 to about 60 degrees, and collect reflected light from the sample through a broad range of angles which may exclude the incident angle. The hand-held portable IR device preferably has the ability to make diffuse reflectance IR spectroscopic measurements (also referred to as an external reflectance IR spectroscopic measurement).

Figure 1A:
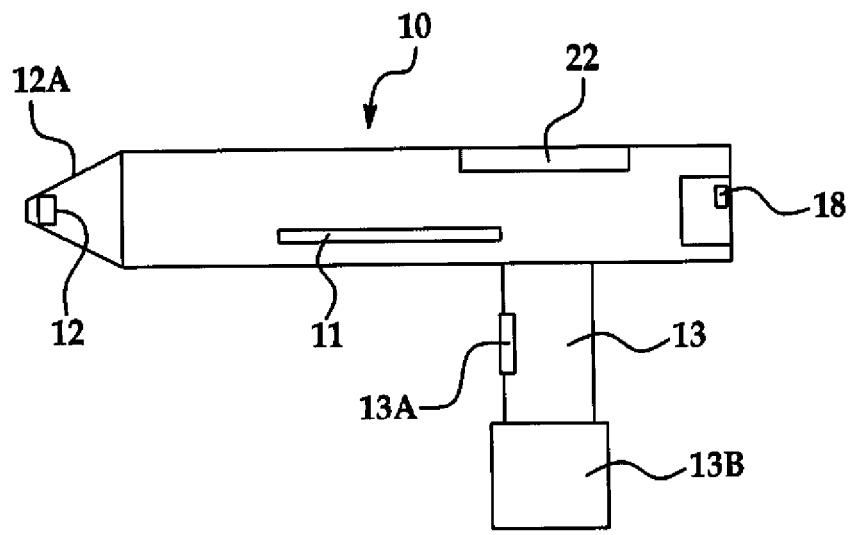
FIG. 1A is a schematic diagram of an exemplary hand-held portable near-IR spectrometer suitably used to make IR spectroscopy measurements according to an embodiment of the invention.

Referring to FIG. 1A is shown a side view of a portable (handheld) IR spectrometer 10 according to an embodiment of the invention. The portable IR spectrometer 10 preferably has the capability of performing near-IR spectroscopy measurements. By the term portable (handheld), is meant an instrument that may be easily carried and picked up and moved about to make IR spectroscopy measurements by an average person, e.g., has a weight of less than about 5 pounds and may be hand-held and aimed (or held against) a location on the measurement surface to make a spot-size measurement.

The portable IR spectrometer 10 also preferably includes a microprocessor and memory (e.g. micro-processor board 11) and may be interfaced (placed in communicated with) with other computing devices (e.g., USB port 18). The portable IR spectrometer 10 may be supplied power by one or more batteries (e.g., 13B in handle portion 13). The portable IR spectrometer 10 is preferably programmable and/or capable of accepting, storing, and executing preprogrammed instructions for carrying out IR spectroscopy measurements. The portable IR spectrometer 10 preferably has the capability to provide incident IR light (energy) and collect reflected IR spectra over an operating wavelength range (e.g., about 1600 nanometers to about 2400 nanometers) and to store the spectra and perform mathematical manipulation of the data comprising the spectra including performing multivariate analysis of the spectra.

In one embodiment, the portable IR spectrometer 10 may have an elongated front portion 12A which includes one or more IR transparent energy windows e.g., 12, for example the front portion 12A may have a nose-like or snout-like (probe) shape, which advantageously aids in the aiming and positioning of the portable IR spectrometer 10 with respect to a measurement surface to make a spot size IR spectroscopy measurement of a pre-defined size. For example, an IR-transparent window 12, may be set back from the surface of the nose portion 12A, which may be placed on or close to the surface of the sample to be measured to produce a known spot-size measurement area, e.g., which may be any size but preferably ranges from an area of about 1 $mm^2$ to about 1 $cm^2$. In some embodiments, the nose portion 12A may be fitted with an interchangeable IR flexible probe (shown in FIG. 1B), including different IR spectrum ranges and/or measurement spot sizes, and may include IR transparent fiber optics.

Figure 1B:
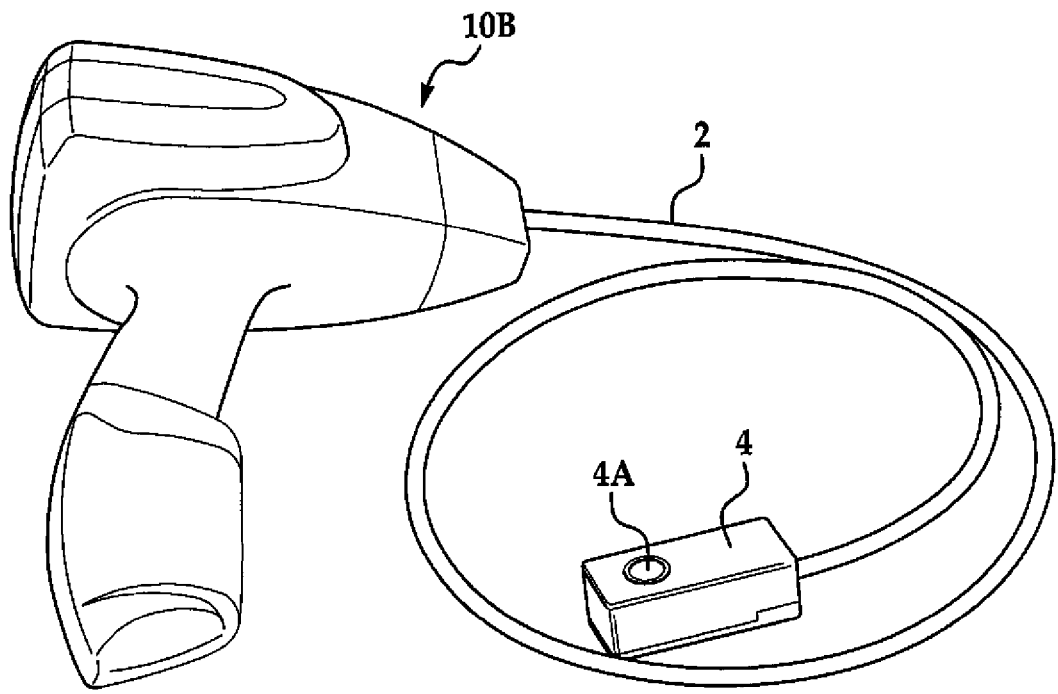
FIG. 1B is a similar hand-held near-IR system with a flexible fiber optic probe.

FIG. 1B shows a near IR hand-held portable IR spectrometer 10B, similar to portable IR spectrometer 10, but with a flexible fiber probe portion 2. The probe shown uses the same reflected light system as typical hand-held near IR systems. The flexible fiber optic probe as an option to be fitted on the nose of the near-IR portable IR spectrometer 10B includes a 0.5 to 2 meter flexible probe portion 2 with protective flexible steel jacket, near IR light source in the probe, e.g., in portion 4, and a trigger device e.g., 4A in the probe including cross hair lines to show measurement position, and rounded bottom corners to accommodate inside diameter of tubing measurements. For example, the bottom portion of the probe 4 may be shaped to accommodate measurement of inner walls of tubes, e.g., in the exemplary embodiment, tubes 5 inches in diameter or larger. The fiber optic probe is optional but is easier to hold and keep steady even on outer surfaces.

The portable IR spectrometer 10 may include a triggering device e.g. 13A on handle portion 13 for triggering an IR spectroscopy or the IR spectroscopy measurement may be alternately triggered e.g., by softkeys on an interactive LCD touchscreen 22. It will be appreciated that the portable IR spectrometer 10 may be of any suitable ergonomic shape to enhance the portability and ease of holding and manipulating the spectrometer to carryout hand-held IR spectroscopy measurements.

The portable IR spectrometer 10 preferably has the ability to store collected IR spectra and perform mathematical manipulation of the data comprising the spectra including multivariate analysis of the spectra. The portable IR spectrometer 10 may include interactive buttons and/or softkeys e.g., on an interactive LCD or LED touchscreen 22, or elsewhere, and may include a textual display to guide the operator through an IR spectroscopy measurement process.

In addition, suitable calibration background reference standard materials and wavelength reference standard materials may be provided for calibrating the IR spectrometer prior to performing IR spectroscopy measurements according to embodiments of the invention.

In one embodiment, an IR spectrometer used to carry out an IR spectroscopy measurement according to the present invention, such as the portable IR spectrometer 10, may be provided and have stored in memory one or more calibration algorithms for IR spectra for use in a subsequent IR spectroscopy measurement and multivariate prediction processes where the IR spectra to be predicted is made with respect to material in a similar condition to an area of the sample with a known level (e.g. baseline including the absence of), the property to be measured, such as the absence of a bond primer film coating on a roughened metallic substrate. For example, it has been found that wavelengths in the near-IR range, e.g., a spectrum of wavelengths from about 1600-2400 are particularly useful for determining the thickness of an organic material such as bond primer on a metallic surface, including a roughened metallic surface. It has been found that the near-IR spectrum is substantially blind to the substrate roughness, which may include surface topology variations having a magnitude on the order of the film coating thickness.

In addition, a previously determined multivariate calibration of IR spectra versus thickness in a film coating may be stored in memory within the IR spectrometer. For example, the predetermined calibration may be determined by calibrating to a plurality of model IR spectra (absorbance and/or reflectance at multiple wavelengths) with a known thickness of model bond primer film coatings from a respective plurality of model samples where the known thickness for each of the model samples is determined by separate and independent measurements, e.g., optical or electron microscopy.

As such, an IR spectrometer, such as portable IR spectrometer 10, may be calibrated such that an in-situ (real-time) analysis of collected IR spectra taken from an actual sample may be performed to determine a thickness of the bond primer film coating. For example, the calibration may be done on an external computer and the resulting calibration model may be down-loaded to the hand-held near-IR system. Preferably, a quantified (numerical) level of the bond primer film coating thickness (or coating weight) may be determined in real-time by a portable IR spectrometer, such as the IR spectrometer 10, and stored and/or output. Additionally or alternatively, a pass/fail type determination (bond primer thickness above or below a threshold numerical value) and resulting indication thereof may stored and/or output.

The portable IR spectrometer 10, or another IR spectrometer used to carry out IR spectroscopy measurements according to embodiments of the invention, may include a computer processor capable of multivariate analysis of the IR spectra or the calibration may be done on an external computer (controller) and the resulting calibration model down-loaded to the hand-held near-IR system. For example, the IR spectrometer (or an associated computer/controller) preferably has the ability to mathematically and statistically correlate and determine changes in a plurality of variables (e.g., IR spectra including reflectance at a plurality of wavelengths) with respect to one or more reference IR spectra. In addition, multivariate statistical approaches may be used to correlate the statistically determined changes in the plurality of variables (e.g., absorbance and/or reflectance at one or more wavelengths) with one or more independently determined second variables (e.g. a change in thickness of an organic material containing coating such as bond primer).

There are many suitable multivariate techniques that may be used to make an IR spectroscopy measurement according to the present invention including, but not limited to, quantification methodologies, such as, partial least squares, principal component regression ("PCR"), linear regression, multiple linear regression, stepwise linear regression, ridge regression, radial basis functions, and the like.

In addition, suitable multivariate statistical approaches include classification methodologies, such as, linear discriminant analysis ("LDA"), cluster analysis (e.g., k-means, C-means, etc., both fuzzy and hard), and neural network ("NN") analysis.

Further, it will be appreciated that there are several data pre-processing methods that may be suitably used to in connection with suitable multivariate statistical approaches including smoothing, taking first and second derivatives of the IR spectra, and peak enhancement methods.

In addition, multivariate analysis of collected IR spectra may include the selection and clustering together of groups of wavelengths on which to perform a regression analysis to determine a corresponding change in the IR spectra (spectrum) (e.g., reflectance) with respect to reference spectra (spectrum). It will be appreciated that an individual IR spectrum may be formed from several IR spectra (e.g., by averaging techniques known in the art). In addition, the raw IR spectra may transformed into second IR spectra by taking first and/or second derivatives and performing smoothing and/or peak enhancement as well as carrying out regression analysis. For example, manipulation the raw IR spectra by smoothing algorithms prior to or following taking a first derivative and then quantifying a degree of change of the IR spectra from a reference spectrum (similarly processed) according to a regression or partial lest squares analysis may be performed.

In addition, the IR spectroscopy measurement process may include collecting reference IR spectra (including calculated absorbance and/or reflectance) which may serve as a baseline from which to determine relative changes in sample IR spectra by multivariate analysis. In addition, various processing methods as are known in the art may be used to form a single IR spectrum from a collection of a plurality of collected IR spectra, including various averaging techniques, for example to improve a signal to noise ratio, prior to carrying out multivariate analysis to determine a change from reference spectrum. It will be appreciated that the change may include a change at one or more wavelengths including clusters of wavelengths.

Figure 2A:
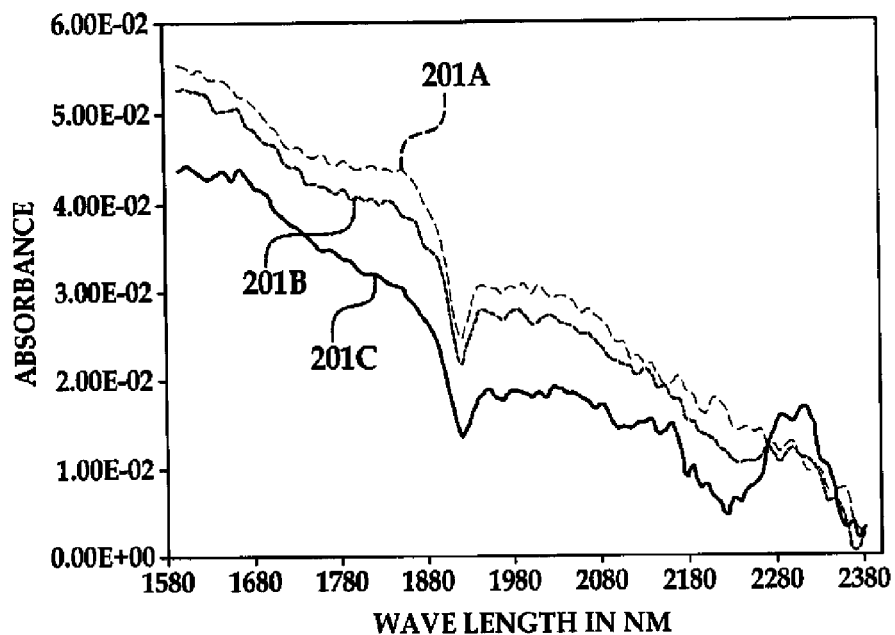
FIG. 2A shows exemplary raw IR spectra used for multivariate calibration according to an embodiment of the invention.
Figure 2B:
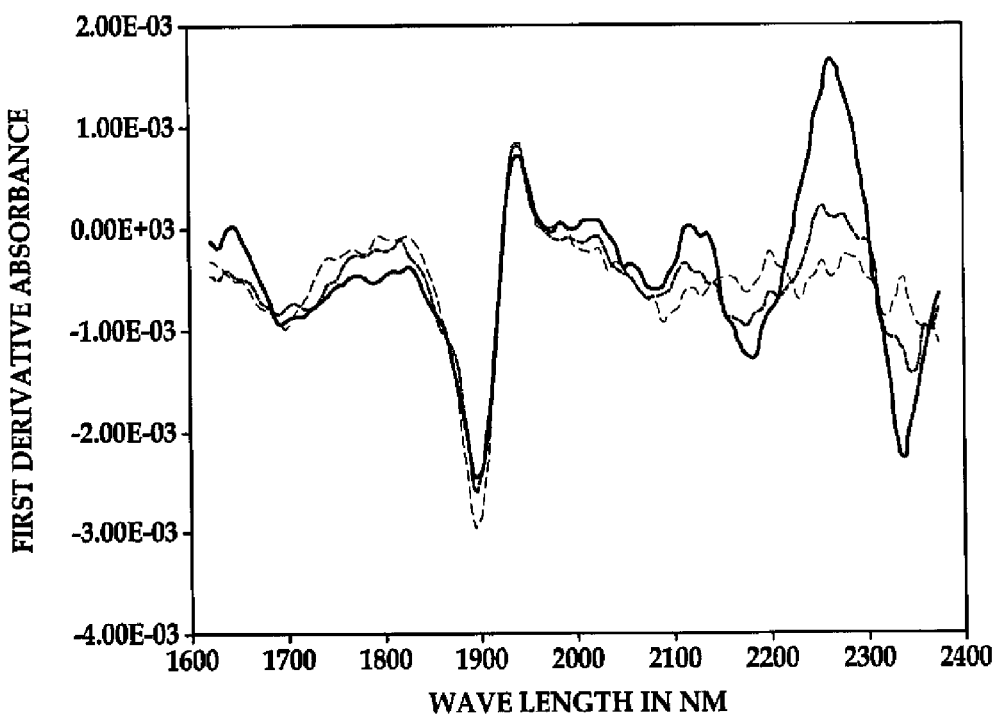
FIG. 2C shows data points for an exemplary conceptual predetermined calibration for a series of several bond primer coating thickness standards. The plot is a typical predicted versus measured plot for multiple near-IR readings on each standard for the calibration of near IR spectra versus film coating thickness according to an embodiment of the invention.
FIG. 2D shows exemplary conceptual regression coefficients vector from the multivariate calibration that is used to predict bond primer thickness for samples in question.

Referring to FIG. 2A is shown a series of exemplary IR spectra 201A, 201B, and 201C following transformation of the raw sample IR spectra with a baseline correction, for example with the base line corrected for near IR data for bond primer on grit blasted Titanium. FIG. 2B shows the same spectra after taking a first derivative, employing a smoothing algorithm (e.g., $1^{st}$ derivative with 7 point smoothing), prior to performing a multivariate calibration which may include multiple spectra on each coating standard, and may use partial least squares to determine the calibration model that can be used to predict the coating thickness or coating weight of samples in question.

Figure 2C:
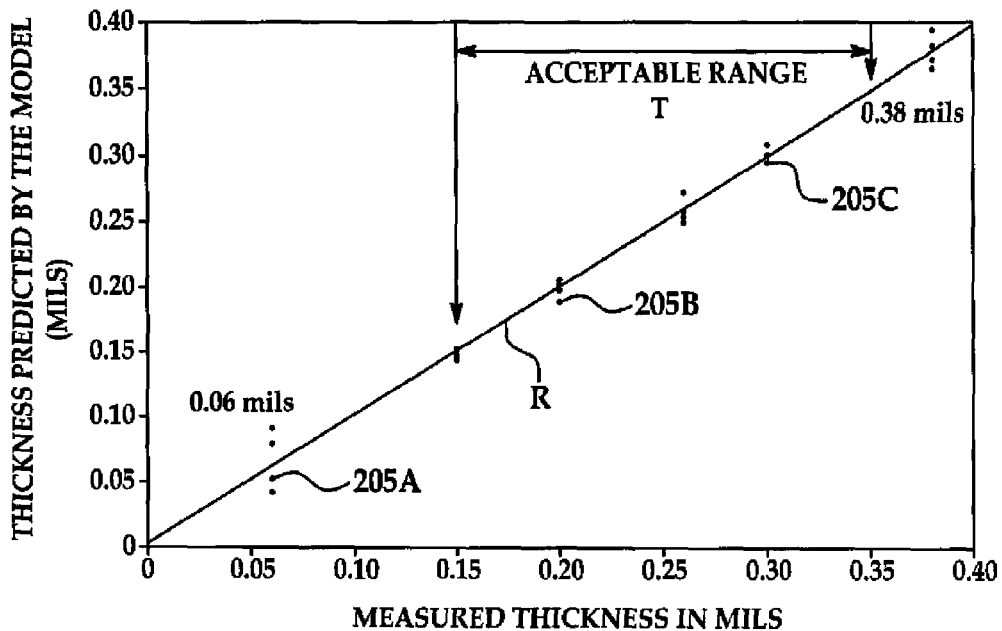

Referring to FIG. 2C is shown a conceptual exemplary calibration plot of a plurality of model near-IR spectroscopy measurements e.g., 205A, 205B, 205C taken from model standards with a known film coating (e.g., bond primer) thickness. The relative changes in absorbance and/or reflectance may be determined for each data point (relative change determined at selected one or more wavelengths) with respect to a reference sample spectrum (which may include an absence of, or a known thickness of, the film coating) according to multivariate analysis. For example, each data point represents a relative change (at one or more wavelengths) in absorbance and/or reflectance compared to a reference IR spectrum e.g., taken from a reference sample without a film coating on a bare substrate or with a known thickness of the film coating. The calibration regression analysis (line R) may be correlated with a separately determined thickness) of the film coating (horizontal axis) e.g., as exemplified by a separate and independent thickness measurement, such as by optical or electron microscopy. Coating weight can also be used for this calibration and it is easier to measure in the process of making standards.

Figure 2D:
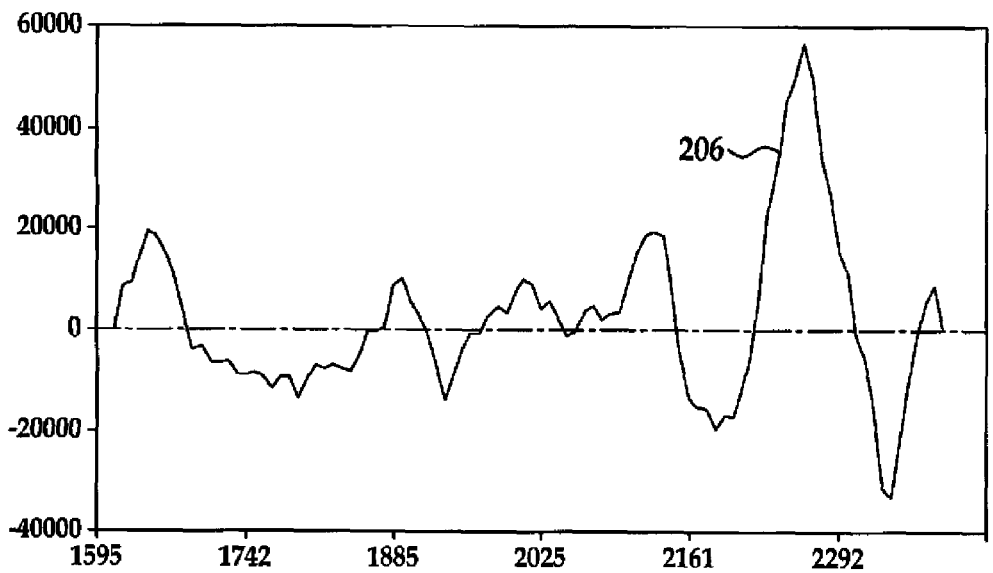

For example, referring to FIG. 2D, shows a conceptual regression coefficients vector 206 from an exemplary multivariate calibration including PLS least squares analysis of near IR spectra that is used to predict the thickness of a film coating of bond primer for samples in question, as explained below.

In one embodiment, the film coating may be a bond primer (organic containing material) that is formed on a metallic surface (substrate). For example, the metallic surface may be a titanium surface, such as a portion of an aircraft which may be bonded by use of the bond primer onto another portion of an aircraft, which may be a different material, including a polymer composite material. In some embodiments, the bond primer may contain chromium (chrome) where amounts of the chromium present may vary depending on the formulation of the bond primer and where the amount of chromium may be important to the performance of the bond primer. In addition, the metallic surface may be treated to form a roughened surface, such as by sand or grit blasting. It will be appreciated that having the correct coating thickness of the bond primer is critical to acceptable bond strength.

For example, creating a multivariate calibration model with a series of known coating standards and using the model to predict the coating thickness or coating weight of samples in question, a quantifiable thickness of the bond primer may be determined. Thus, the quality or acceptability of the bond primer surface may be advantageously determined in real time with a hand-held portable IR spectrometer prior to bonding taking place in a manufacturing or maintenance process.

It will be appreciated that the method of the present invention is particularly advantageous when used to measure film coating thicknesses on roughened or uneven metal surfaces. For example, the roughness of the metal surface may include having variations in the surface topology up to about the thickness of the film coating, e.g., up to about 1 mil (0.001 inch).

For example, referring to FIG. 2C, is shown an exemplary conceptual predetermined calibration and prediction plot R representing a model validation method that leaves out one sample to make a model and uses that model to predict the sample omitted. This is done for each sample in order to build a predicted versus measured plot for FIG. 2C. The predetermined multivariate calibration automatically correlates the changes in IR spectroscopy measurements e.g., 205A, 205B, 205C, (where the relative change on the vertical axis in absorbance and/or reflectance is shown at a selected wavelength or group of wavelengths) and with the coating thickness or coating weight of the standards measured for the model.

Still referring to FIG. 2C, in one embodiment, a thickness range T may be imposed on the predetermined correlation R, so that the IR spectroscopy measurements e.g., 205B and 205C can then be determined (estimated) to have a thickness within the proper range or thickness range T on the horizontal axis. For example, in one embodiment, an acceptable range for the bond primer thickness is in a range of about 0.15 to about 0.35 mils. For example, in the exemplary sample IR spectroscopy measurements, e.g., 205B and 205C show a thickness within the thickness range T, and the thickness of the bond primer may be determined to be acceptable and the operator of the IR spectrometer notified by an audible and/or visual indication. Thus, the measurements 205B and 205C are determined in-situ and in real-time determined to represent an acceptable bond primer thickness following IR spectroscopic collection, multivariate prediction, and comparison to a predetermined thickness range T. On the other hand, measurement 205A may be determined to have an unacceptable bond primer thickness and the operator similarly notified.

It will be appreciated that an IR spectrometer used to make the measurement, such as hand-held portable IR spectrometer 10, may be programmed to keep track of a running average of estimated thickness according to several individual IR spectroscopic measurements made over a defined measurement area to determine whether an averaged thickness of the film coating (e.g., bond primer) over the measurement area is acceptable (e.g., above the threshold thickness range T) or unacceptable (e.g., below the threshold thickness range T).

In practice it has been found that the film thickness determination according to IR spectroscopy according to preferred embodiments of the invention for film thicknesses of about 0.1 to about 1 mil (0.001 inch) has an accuracy of about plus or minus 0.01 mil with respect to a separately performed thickness measurement (e.g., having an accuracy of equal to or greater than plus or minus 0.01 mil).

In one embodiment, the quantifiable level of the film coating thickness may include a separate spectroscopic measurement, such as in the UV and/or visible range of wavelengths that may be correlated with a separately and independently measured film coating thickness.

Figure 3:
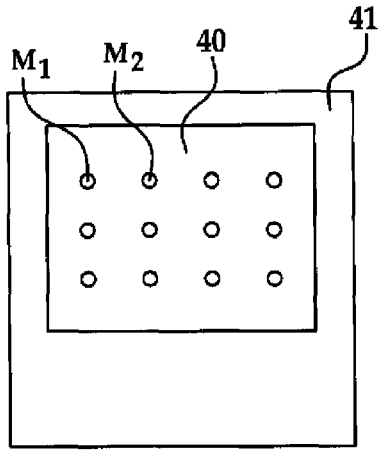
FIG. 3 shows an exemplary IR spectroscopy spot measurement process to map a film coating surface according to an embodiment of the invention.

Referring to FIG. 3, an exemplary IR spectroscopy measurement process is shown including an exemplary mapping of a film coating 40 on a roughened metallic surface 41 (underneath film coating 40). For example, following calibrating the IR spectrometer 10, a plurality of IR spectroscopy spot measurements e.g., M1, M2 (e.g., defined spot size of from 1 $mm^2$-10 $mm^2$) may be made sequentially or randomly over a predetermined area of the film coating surface. A thickness map of the sample measurement area may be generated by mapping a determined thickness with respect to each spot IR spectroscopy measurement and/or a running average thickness may be sequentially determined over a defined measurement area for several IR spectroscopy measurements. It will be appreciated that the IR spectroscopy measurement spots e.g., M1, M2, may be any shape and where the noted spot sizes approximate a defined IR spectroscopic measurement area for an individual IR spectroscopy measurement.

Figure 4:
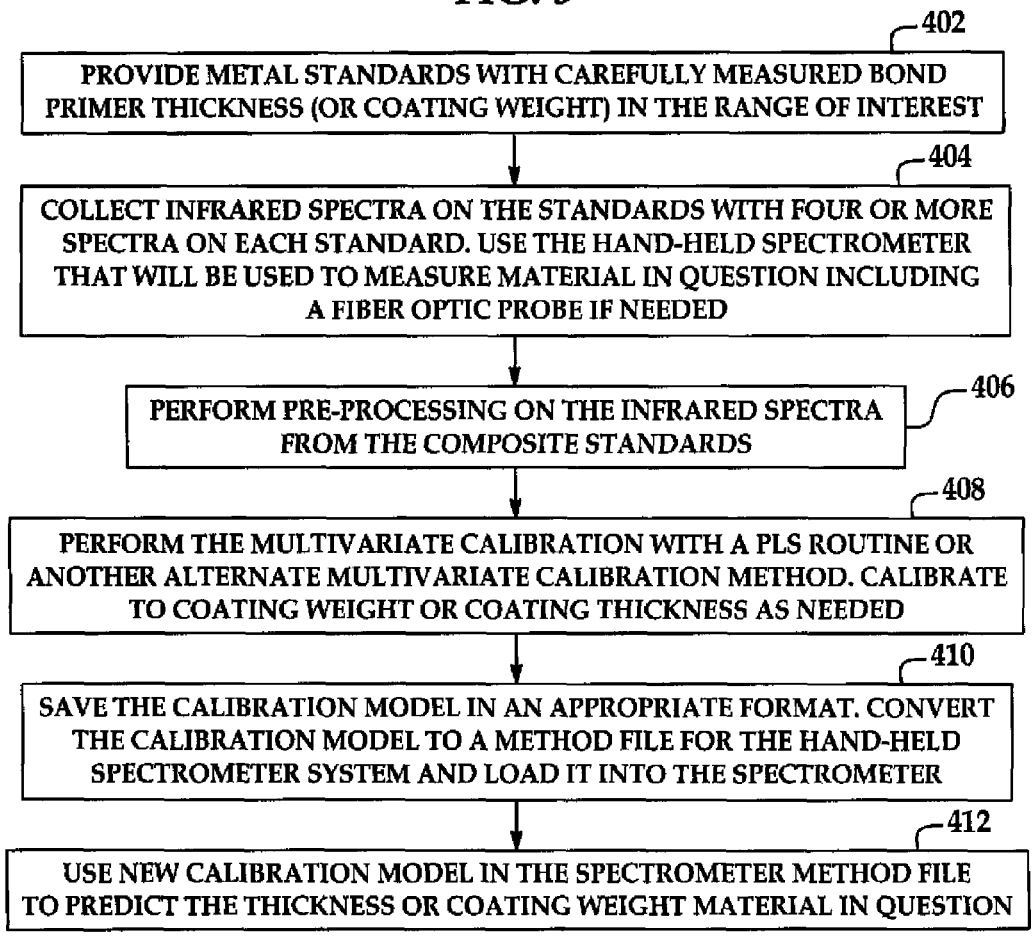
FIG. 4 is an exemplary process flow diagram including embodiments of the invention.

In an exemplary IR spectroscopy measurement process, referring to FIG. 4, in step 402 a series of coating weight or coating thickness standards are obtained for use in the calibration. In step 404 multiple IR spectra are collected on each standard (e.g., over near-IR wavelength range 1600-2400 nm) e.g., which may include using a reference sample with a bare substrate (e.g., metal) similar in surface topology (roughness) to the measurement samples to make an appropriate reference for the measurements. The coating thickness or weight standards must have a known thickness or coating weight of the film coating on the substrate. In step 406, the data pre-processing is performed on the spectra of the calibration standards in order to prepare the spectra for a good calibration model.

In step 408, a multivariate calibration model is made with the sample spectra and the known film coating thicknesses or coating weight determined by an independent thickness or weight measurements.

In steps 410 and 412, the calibration model is saved in a format that is useful for the hand-held spectrometer and it is down-loaded into the spectrometer system for use in prediction coating thickness or coating weight for samples in question.

Figure 5:
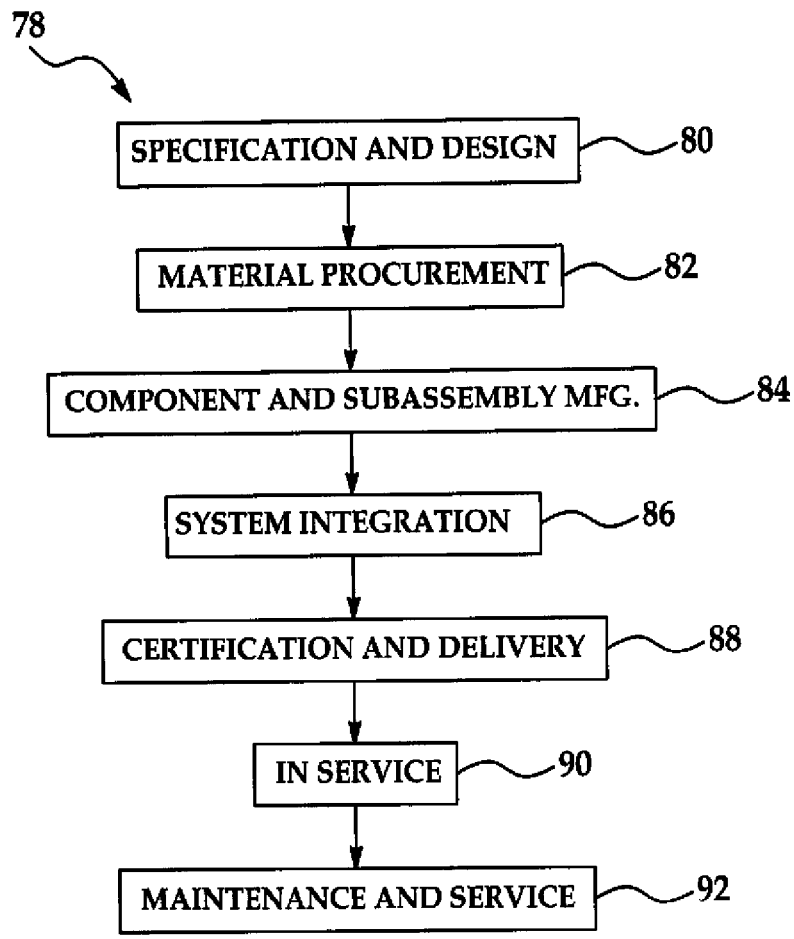
FIG. 5 is a flow diagram of an aircraft and service methodology according to an embodiment of the invention.
Figure 6:
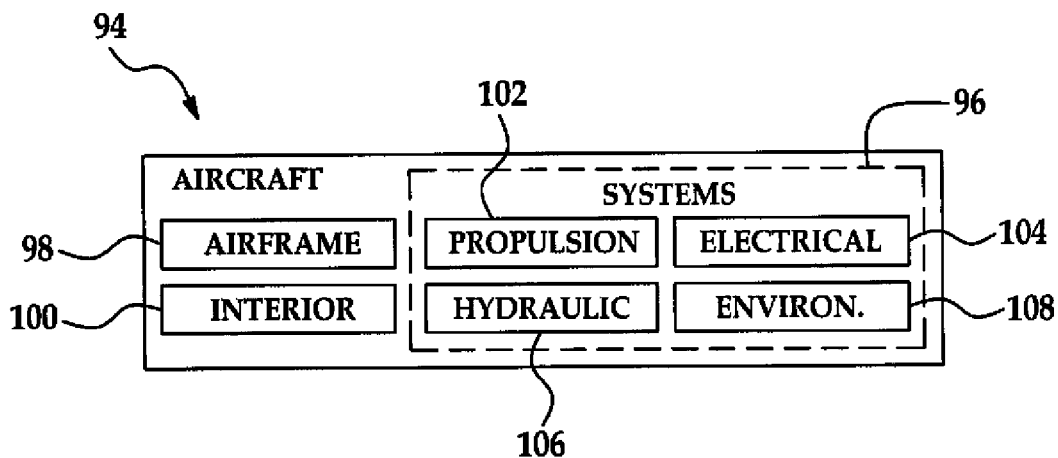
FIG. 6 is a block diagram of an aircraft according to an embodiment of the invention.

Referring next to FIGS. 5 and 6, embodiments of the disclosure may be used in the context of an aircraft manufacturing and service method 78 as shown in FIG. 5 and an aircraft 94 as shown in FIG. 6. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 6, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of determining a film coating thickness on a substrate comprising:
    irradiating said film coating with infrared energy over a spectrum of wavelengths, said spectrum comprising multiple wavelengths over a wavelength range of from about 1600 to about 2400 nanometers;
    detecting said infrared energy reflected from said film coating on said substrate over said spectrum of wavelengths without filtering said spectrum;
    performing multivariate analysis on the spectrum of said reflected infrared energy;
    comparing results of said multivariate analysis with a predetermined correlation between model infrared energy spectra comprising said spectrum of wavelengths collected from a plurality of model film coatings, said model film coatings each having a known film coating thickness or weight; and,
    determining said film coating thickness based on said predetermined correlation.

2. The method of claim 1, wherein said multivariate analysis comprises multivariate statistical approaches to determine changes in absorbance and/or reflectance values at selected groups of wavelengths comprising said spectrum of wavelengths, said changes with respect to a reference spectrum.

3. The method of claim 1, wherein said film coating comprises an organic containing material and the substrate comprise a metallic surface.

4. The method of claim 1, wherein said film coating comprises a bonding primer.

5. The method of claims 1, wherein said substrate comprises a roughened metallic surface, said roughened surface comprising a surface topology variation up to about said film coating thickness.

6. The method of claim 1, wherein said film coating thickness is determined with an accuracy of up to plus or minus 0.01 mil.

7. The method of claim 1, wherein said step of irradiating said film coating is preceded by collecting a reference spectrum over said spectrum of wavelengths from a reference sample wherein said film coating is absent or present at a known thickness or weight.

8. The method of claim 1, wherein said steps of irradiating and detecting are performed by a hand-held portable IR spectrometer.

9. The method of claim 1, wherein said steps are performed by a hand-held portable IR spectrometer equipped with a flexible fiber optic probe.

10. The method of claim 1, wherein said steps of irradiating and detecting are performed over a pre-determined area on said film coating.

11. The method of claim 1, wherein said steps comprise a process selected from the group consisting of aircraft manufacturing, aircraft assembly, aircraft maintenance, and aircraft repair.

12. A method of determining a film coating thickness on a metallic substrate comprising:
    collecting a reference spectrum over a spectrum of infrared wavelengths from a reference sample wherein said film coating is absent or present at a known thickness or weight, said spectrum of infrared wavelengths comprising multiple wavelengths over a wavelength range of from about 1600 to about 2400 nanometers;
    irradiating said film coating on said substrate with infrared energy over said spectrum of wavelengths;
    detecting said infrared energy reflected from said film coating on said substrate over said spectrum of wavelengths without filtering said spectrum;
    performing multivariate analysis on the spectrum of said reflected infrared energy;
    comparing results of said multivariate analysis with a predetermined correlation between model infrared energy spectra comprising said spectrum of wavelengths collected from a plurality of model film coatings, said model film coatings each having a known thickness or weight; and,
    determining said thickness of said film coating based on said predetermined correlation.

13. The method of claim 12, wherein said multivariate analysis comprises multivariate statistical approaches to determine changes in absorbance and/or reflectance values at selected groups of wavelengths comprising said spectrum of wavelengths, said changes with respect to a reference spectrum.

14. The method of claim 12, wherein said film coating comprises an organic containing material.

15. The method of claim 12, wherein said film coating comprises a bonding primer.

16. The method of claims 12, wherein said metallic substrate comprises a roughened surface, said roughened surface comprising a surface topology variation up to about said film coating thickness.

17. The method of claims 12, wherein said film coating thickness is determined to an accuracy of up to plus or minus 0.01 mil.

18. The method of claim 12, wherein said steps are performed by a hand-held portable IR spectrometer.

19. The method of claim 12, wherein said steps of irradiating and detecting are performed over a pre-determined area on said film coating.

20. The method of claim 12, wherein said steps comprise a process selected from the group consisting of aircraft manufacturing, aircraft assembly, aircraft maintenance, and aircraft repair.

21. A method of determining a film coating thickness on a roughened metallic substrate using a portable hand-held spectrometer comprising:
- collecting a reference spectrum over a spectrum of infrared wavelengths from a reference sample wherein said film coating is absent or present at a known thickness or weight, said spectrum of infrared wavelengths comprising multiple wavelengths over a wavelength range of from about 1600 to about 2400 nanometers;
- positioning said portable hand-held spectrometer to irradiate and detect reflected infrared energy over said spectrum of infrared wavelengths over a pre-determined area on said film coating;
- irradiating said film coating on said metallic substrate with infrared energy over said spectrum of wavelengths;
- detecting said infrared energy reflected from said film coating on said metallic substrate over said spectrum of wavelengths without filtering said spectrum;
- performing multivariate analysis on the spectrum of said reflected infrared energy;
- comparing results of said multivariate analysis with a predetermined correlation between model infrared energy spectra comprising said spectrum of wavelengths collected from a plurality of model film coatings, said model film coatings each having a known thickness or weight; and,
- determining said thickness of said film coating based on said predetermined correlation.

\* \* \* \* \*